(12) United States Patent
Dodds et al.

(10) Patent No.: US 7,470,442 B2
(45) Date of Patent: Dec. 30, 2008

(54) CONFECTIONARY COMPOSITIONS WITH MAGNOLIA BARK EXTRACT

(75) Inventors: Michael W. J. Dodds, La Grange Park, IL (US); James Roy Maxwell, Chicago, IL (US); Michael J. Greenberg, Northbrook, IL (US); Minmin Tian, Naperville, IL (US)

(73) Assignee: GIC Innovations Company, Chicago, IL (US)

( * ) Notice: Subject to any disclaimer, the term of this patent is extended or adjusted under 35 U.S.C. 154(b) by 35 days.

(21) Appl. No.: 11/602,166

(22) Filed: Nov. 17, 2006

(65) Prior Publication Data

US 2007/0183990 A1    Aug. 9, 2007

Related U.S. Application Data

(60) Provisional application No. 60/742,476, filed on Dec. 2, 2005.

(51) Int. Cl.
*A61K 36/00* (2006.01)

(52) U.S. Cl. .................................................. 424/775
(58) Field of Classification Search .................. None
See application file for complete search history.

(56) References Cited

U.S. PATENT DOCUMENTS

| | | | |
|---|---|---|---|
| 4,547,361 A | 10/1985 | Steltenkamp et al. | |
| 4,820,544 A | 4/1989 | Barcelon et al. | |
| 5,939,050 A | 8/1999 | Iyer et al. | |
| 5,948,430 A | 9/1999 | Zerbe et al. | |
| 6,248,309 B1 | 6/2001 | Iyer et al. | |
| 6,280,751 B1 | 8/2001 | Fletcher et al. | |
| 6,284,264 B1 | 9/2001 | Zerbe et al. | |
| 6,495,512 B1 | 12/2002 | White et al. | |
| 6,500,409 B1 | 12/2002 | Scheri et al. | |
| 6,582,735 B2 | 6/2003 | Stogniew et al. | |
| 6,703,000 B2 | 3/2004 | Ning et al. | |
| 6,719,962 B2 | 4/2004 | Day et al. | |
| 6,726,897 B2 | 4/2004 | Lawlor et al. | |
| 7,025,983 B2 | 4/2006 | Leung et al. | |
| 2002/0131990 A1 | 9/2002 | Barkalow et al. | |
| 2004/0081713 A1* | 4/2004 | Maxwell et al. | ............. 424/769 |
| 2005/0008690 A1 | 1/2005 | Miller | |

FOREIGN PATENT DOCUMENTS

| | | |
|---|---|---|
| CN | 1094895 A | 11/1994 |
| CN | 1096694 | 12/1994 |
| CN | 1096699 | 12/1994 |
| CN | 94116766.6 | 1/1996 |
| CN | 1141194 A | 1/1997 |
| CN | 1073410 C | 10/2001 |
| GB | 1311060 | 3/1973 |
| JP | 84-175422 | 10/1984 |
| KR | 2002-0003413 | 1/2002 |
| WO | WO 97/35599 | 10/1997 |
| WO | WO 99/51093 | 10/1999 |
| WO | WO 01/82922 A1 | 11/2001 |
| WO | WO 0185116 A * | 11/2001 |
| WO | WO 02/072114 A2 | 9/2002 |
| WO | WO 02/091848 A1 | 11/2002 |
| WO | WO 2004/000235 | 12/2003 |

OTHER PUBLICATIONS

Sharma A. et al., 2005, *Oral Microbiology and Immunology* 20: 39-42.

* cited by examiner

*Primary Examiner*—Christopher R Tate
*Assistant Examiner*—Deborah A. Davis
(74) *Attorney, Agent, or Firm*—Brinks Hofer Gilson & Lione

(57) ABSTRACT

A confectionary composition and a method for oral care that includes Magnolia Bark Extract in combination with a surface active agent. The effectiveness of Magnolia Bark Extract in inhibiting biofilm formation in the oral cavity is increased by a synergistic combination of the Magnolia Bark Extract with a surface active agent in an oral cavity delivery agent, such as confectionary, a lozenge, a candy, and a tablet.

18 Claims, No Drawings

CONFECTIONARY COMPOSITIONS WITH MAGNOLIA BARK EXTRACT

RELATED U.S. APPLICATION

This application claims priority to U.S. provisional patent application Ser. No. 60/742,476, filed Dec. 2, 2005.

TECHNICAL FIELD

The present invention relates, in general, to confectionary compositions and, more particularly, to confectionary compositions containing Magnolia Bark Extract for oral care, and to methods of making the confectionary compositions.

BACKGROUND

There is considerable consumer demand for products that freshen breath and kill bacteria in the mouth. An oral product with breath freshening and bactericidal benefits is a convenient delivery for oral cleansing in the oral cavity and freshening breath. Bacteria in the oral cavity, particularly on the tongue, can generate volatile sulfur compounds, which are a major cause of bad breath. Of course, breath freshening is a very important part of everyday life.

In order to facilitate proper oral hygiene, oral cleansing and breath freshening practices should be conducted repeatedly throughout the day. However, oral cleansing and breath freshening may be difficult or inconvenient at times, depending on the nature of the breath freshening desired and the situation in which the breath freshening must occur. Brushing, flossing, cleaning your tongue and gargling using a variety of devices and compositions are common oral care practices well-suited for the privacy of one's home. But, such devices and compositions are less convenient to use away from the home where bathroom facilities might be scarce, unavailable or unsanitary.

Dental plaque is a microbial deposit that forms on teeth within a short time of brushing. It has been described by researchers as a soft, concentrated mass consisting mainly of a large variety of bacteria together with a certain amount of cellular debris which develops within a short time of refraining from tooth brushing. Dental plaque is not removed by rinsing with water. More recently researchers have recognized that plaque is a microbial biofilm. Dental plaque has been described as a diverse community of micro-organisms found on the tooth surface as a biofilm. The biofilm is embedded in an extracellular matrix of polymers that originate from both the tooth surface and the microbial organisms. It is generally recognized that a reduction in dental plaque promotes clean teeth, fresh breath, and healthy gums. The dental plaque biofilm, however, is very resistant to antimicrobial agents.

Antimicrobials agents that have been shown to have definite plaque-reducing abilities include chlorhexidine, cetylpyridinium chloride (CPC), Triclosan and Delmopinol. These are all medicinal and non-natural agents. Essential oils such as thymol, Eucalyptol, methyl salicylate, and menthol along with other essential oils in an alcohol-based vehicle have also been found to reduce plaque. While thymol is most effective in reducing plaque, it has a disagreeable taste. Generally, these oils benefit from the presence of an alcohol to facilitate their solubility and penetration of the plaque biofilm. While suitable for oral treatments, such as mouthwashes, high concentrations of alcohols can leave a bitter aftertaste in oral compositions, such as lozenges, tablets, confectionaries, and the like.

An active ingredient, or a combination of active ingredients, that can provide the benefits of either removing plaque, preventing or slowing down plaque formation, or that has an anti-inflammatory effect that would help maintain the healthy state of the gums would promote healthy gums and fresh breath. It is known to incorporate active agents into pressed tablets for the purpose of providing oral benefits including breath freshening and bactericidal properties. Such systems have the advantage of providing rapid, effect, and convenient delivery.

BRIEF SUMMARY

The present invention is directed towards a breath freshening composition that can be used in different confectionery products such as hard candies, pressed mints, tablets, and lozenges. One aspect of the present invention is directed towards the use of comestible products for humans, such as tablets, lozenges, chewing gums, hard candies, and pressed mints, or comestible products for animals, such as dog biscuits, wherein the comestible products contain a breath freshening composition of the present invention.

In accordance with the present invention it has been unexpectedly discovered that Magnolia Bark Extract in combination with certain surface active agents is synergistically effective in inhibiting the growth of plaque-causing bacteria. The combination of Magnolia Bark Extract and selected surface active agents shows enhanced antiplaque growth activity in excess of either Magnolia Bark Extract or the surface active agent alone.

The present invention further relates to confectionary compositions containing Magnolia Bark Extract in combination with a surface active agent intended for bactericidal and breath freshening properties. More specifically, the present invention relates to an oral cavity delivery agent, such as a dentifrice, confection, lozenge, pressed tablet, or other comestible product containing an effective amount of Magnolia Bark Extract in combination with a surface active agent, by which the inventive composition effectively inactivates or kills oral bacteria and freshens breath through the consumption of the dentifrice, confection, lozenge, pressed tablet, or other comestible product. The surface active agent is added to the pressed tablet to synergistically increase the effectiveness of the Magnolia Bark extract.

In one aspect of the invention a confectionary composition for freshening the breath of consumers of the pressed tablet includes an oral cavity delivery agent and an effective amount of an antimicrobial agent comprising a synergistic ratio of Magnolia Bark Extract and surface active agent, wherein the synergistic ratio is at least about 1 part Magnolia Bark Extract to 1 part surface active agent.

Suitable surface active agents include salts of potassium, ammonium, or sodium. Sodium salts include anionic surfactants, such as alkyl sulfates, including sodium lauryl sulfate, sodium laureth sulfate, and the like. Other sodium salts include sodium lauroyl sarcosinate, sodium brasslate, and the like. Suitable ammonium salts include ammonium lauryl sulfate, ammonium laureth sulfate, ammonium lauroyl sarcosinate, ammonium brasslate, ammonium cocamidopropyl betaine, and the like. Other suitable surface active agents include emulsifiers, which can be fatty acids (for example, stearic, palmitic, oleic, and linoleic acids), their salts, glycerol monostearate, glycerol triacetate, lecithin, mono and triglycerides, and acetylated monoglycerides. As will be described below, several suitable surface active agents also show some bactericidal (germ-kill) properties on their own.

In another aspect of the invention, the oral cavity delivery agent is a comestible product including but not limited to hard candy, chewing candy, filled candy and pressed tablets. A comestible product for freshening the breath of consumers includes at least one of a sugar or a sugar alcohol and an effective amount of an antimicrobial agent comprising a synergistic ratio of Magnolia Bark Extract and surface active agent. The synergistic ratio is at least about 1 part Magnolia Bark Extract to 1 part surface active agent.

In a further aspect of the invention, a method of oral cleansing includes applying a confectionary composition to the oral cavity, where the confectionary composition includes an effective amount of an antimicrobial agent where the antimicrobial agent comprises a synergistic ratio of Magnolia Bark Extract and surface active agent, wherein the synergistic ratio is at least about 1 part Magnolia Bark Extract to 1 part surface active agent.

DETAILED DESCRIPTION

Confectionary compositions can be used as vehicles for delivering components to the oral cavity which provide benefits such as breath freshening and bactericidal properties. Such systems have the advantage of providing a consumer with a convenient and inexpensive method for maintaining oral health and fresh breath throughout the course of the day.

The present invention incorporates Magnolia Bark Extract in a confectionary composition, as the active component for breath freshening and oral bactericidal benefits. Magnolia Bark Extract is known to have bactericidal and fungicidal properties. For example, magnolol and honokiol are two components in Magnolia Bark Extract with antimicrobial activity.

The invention is further directed to a method of reducing or eliminating microorganisms present in the oral cavity, comprising masticating in the oral cavity a comestible product which contains confectionary composition comprising Magnolia Bark Extract and a surface active agent. Suitable confectionary products include tablets, lozenges, hard and chewy candies, pressed mints, toffees, caramels, cremes, syrups, chocolates and nougats, which contain Magnolia Bark Extract and a surface active agent according to the present invention.

The term "masticating" includes operations by which an edible product (confectionary composition) is wholly or partially consumed while it is being held in the mouth, such as by chewing, sucking, or dissolving. Holding the product in the mouth for longer periods of time is expected to be associated with greater reduction of the microorganisms present in the oral cavity. Suitably effective periods of time for mastication range from 3-5 minutes, up to 20-30 minutes.

The Magnolia Bark Extract used in the present invention may be obtained from O'Laughlin Industries, Co. LTD, Guang Zhou Masson Pharmaceutical Co., or Honsea Sunshine Bioscience and Technology Co. The Magnolia Bark Extract is obtained in the form of powder. The Magnolia Bark Extract is dissolved with the flavor and may be warmed to dissolve prior to making the oral product. Magnolia Bark Extract can be formulated using standard formulation techniques into gel caps, teas, tablets, etc.

While it is relatively easy to kill bacteria in solutions, the plaque biofilm is a complex environment that provides protection from environmental threat to the bacteria, as well as synergies between bacterial species (A. Sharma, S. Inagaki, W. Sigurdson, H. K. Kuramitsu, 2005, Synergy between *Tannerella forsythia* and *Fusobacterium nucleatum* in biofilm formation, *Oral Microbiology and Immunology* 20: 39-42). Therefore, compared to a simple germ kill test, it is much harder to show actual efficacy against established plaque by an anti-microbial agent. Diffusion into the biofilm is limited, and bacteria within the bulk of the biofilm are protected from exposure to the agent by extracellular material, such as the glucan and dextran polysaccharides. It is, therefore, arguably easier to prevent formation of plaque than it is to remove an established plaque.

In accordance with the present invention, the antimicrobial effects of Magnolia Bark Extract are enhanced through the combination of Magnolia Bark Extract with a surface active agent. Although not intending that the invention be limited to any particular theory, it is believed that the combination of a surface active agent with an effective amount Magnolia Bark Extract can provide a confectionary composition, for example a pressed tablet, that promotes the reduction of biofilms in dental plaques and in other areas of the oral cavity, such as the tongue. It is believed that the combination of Magnolia Bark Extract and a suitable surface active agent may prevent bacterial attachment to the acquired pellicle. Such a pressed tablet can slow down or prevent plaque accumulation. Further, the pressed tablet of the invention can be effective in the removal of existing plaque in combination with enzymes, additional surfactants, abrasives or combinations thereof.

A preferred surface active agent is one that increases the solubility of Magnolia Bark Extract and that can be used as a food additive. Suitable surface active agents include but are not limited to common surfactants, soaps, wetting agents, and emulsifiers. Some examples of surfactants include but are not limited to salts of potassium, ammonium, or sodium. Sodium salts include anionic surfactants, such as such as alkyl sulfates, including sodium lauryl sulfate, sodium laureth sulfate, and the like. Other sodium salts include sodium lauroyl sarcosinate, sodium brasslate, and the like. Suitable ammonium salts include ammonium lauryl sulfate, ammonium laureth sulfate, ammonium lauroyl sarcosinate, ammonium brasslate, ammonium cocamidopropyl betaine, and the like. Other suitable surface active agents include emulsifiers, which can be fatty acids (for example, stearic, palmitic, oleic, and linoleic acids), their salts, glycerol monostearate, glycerol triacetate, lecithin, mono and triglycerides, and acetylated monoglycerides. As will be described below, several suitable surface active agents also show some bactericidal (germ-kill) properties on their own.

The pressed tablet can also include additional breath freshening or oral health ingredients, which can be anti-microbial ingredients. Further, the additional breath freshening or oral health ingredients can comprise food acceptable salts of zinc or copper, cooling agents, pyrophosphates or polyphosphates, and the like.

The invention also includes a treatment method for reducing the number or activity of bacteria in the oral cavity of a consumer comprising the steps of providing a pressed tablet comprising Magnolia Bark Extract in an amount sufficient to kill or deactivate oral bacteria in combination with a surface active agent and causing a person in need of the treatment to consume the pressed tablet whereby the bacteria in the oral cavity of the person is reduced or inactivated by the treatment.

In one form, the pressed tablet is formulated with an oral cavity delivery agent to deliver at least about 0.001% to about 2.0% concentration of Magnolia Bark Extract to the oral cavity. In another form, the pressed tablet is formulated with an oral cavity delivery agent to deliver at least about 0.01% concentration of Magnolia Bark Extract to the oral cavity. One or more surface active agents are added to the pressed tablet so as to enhance the effectiveness of the pressed tablet in the delivery of an effective amount to the oral cavity.

In accordance with one embodiment of the invention, one or more surface active agents are present in the pressed tablet in a concentration range of about 0.001% to about 2.0%. In the pressed tablet, Magnolia Bark Extract is combined with a surface active agent in a synergistic ratio that provides enhanced germ-kill effectiveness. The synergistic ratio ranges from about 1 part Magnolia Bark Extract to 1 part surface active agent up to about 4 parts Magnolia Bark Extract to 1 part surface active agent. One particularly effective surface active agent is sodium lauryl sulfate, and a particularly effective synergistic composition is about 2 parts Magnolia Bark Extract to 1 part sodium lauryl sulfate.

Given that Magnolia Bark Extract is a hydrophobic compound, there are several oral cavity delivery agents that may be used to enhance the release of the Magnolia Bark Extract from the pressed tablet. In a pressed tablet, the confectionary composition base is hydrophobic, which also inhibits the release of the Magnolia Bark Extract. In the various embodiments of the inventive confectionary composition, the Magnolia Bark Extract is combined with a surface active agent and may be encapsulated, spray dried, or formulated into a coating, or combinations thereof in order to facilitate release of the Magnolia Bark Extract into the oral cavity.

To evaluate the effectiveness of Magnolia Bark Extract, in vitro tests were conducted with three subgingival plaque bacteria associated with oral malodor. The Minimum-Inhibitory-Concentrations (MIC) study protocol is as follows. Chlorhexidine was used as a positive control and sterile water was used as a negative control. Menthol and Tween 80 was used as a solvent for Magnolia Bark Extract. Tween 80 is the common name for Polysorbate 80. Ninety-six-well microtiter plates were used for this study. Each well contained $5 \times 10^5$ colony forming units/ml of bacteria, serially diluted agents and bacterial growth medium. All bacterial cultures were incubated at 37° C. and stationary. Bacterial growth was estimated spectrophotometrically at 660 nm, after 48 hours. The MIC for each test bacteria was defined as the minimum concentration of test compound limiting turbidity to less than 0.05 absorbance at 660 nm.

The Minimum-Bactericidal-Concentrations (MBC) were determined using the 96-well microtiter plate serial dilutions as described above for MIC studies. Serial dilutions of cultures in wells showing no visible growth were performed and 10 microliters of culture were plated in triplicate on blood agar plates. Viable colonies were scored after incubation of the plates for 48 hours at 37° C. For each test bacterium, the number of colony forming units/ml (CFU/ml) was determined in the initial inoculum. The MBC was defined as the lowest concentration of a test compound that killed at least 99.9% of the cells present in the initial inoculum.

The results of the studies performed to obtain MIC and MBC of Magnolia Bark Extract (MBE) are as follows. Against *Streptococcus mutans* a Magnolia Bark Extract of 90% had an MIC of 15.62 µg/ml. For *Porphyromonas gingivalis*, the 90% Magnolia Bark Extract had an MIC of 3.91 µg/ml, and the 65% Magnolia Bark Extract had an MIC of 7.82 µg/ml. For *Fusobacterium nucleatum* the 90% Magnolia Bark Extract had an MIC of 3.91 µg/ml and an MBC of 7.82 µg/ml. Against the same organism, the 65% Magnolia Bark Extract had an MIC and MBC of 7.82 µg/ml. Chlorhexidine was the positive control and produced an MIC and MBC of 1.25 µg/ml for all three bacteria. The solvent consisting of water with 10% methanol and 3.8% Tween 80 had no noticeable growth inhibitory effects on any of the three bacteria in the study.

It is also known that Magnolia Bark Extract is effective against *Actinobacillus actinomyecetemcomitans, Prevotella intermedia, Micrococcus luteus*, and *Bacillus subtilis, Veillonella disper, Capnocytophaga gingivalis*, and periodontal microorganisms.

Further to the results described above, the effect of Magnolia Bark Extract on biofilm formation and removal was compared with different herbal and natural ingredients. Comparative testing was performed using green tea extract, Oolong tea extract, Licorice, and Magnolia Bark Extract. The comparative testing included determining the solubility in water, ethanol, water:ethanol mixtures and other solvents (for example, Tween in water), MIC for growth of *S. mutans*, MIC for formation of *S. mutans* biofilm in 96-well plates, and the effect on detachment of *S. mutans* biofilm.

The green tea was soluble in water; all other substances were found to be soluble in a 2:1 water:ethanol mixture. Magnolia Bark Extract was also soluble in 0.01 µl of 50% Tween 80 in water.

To further evaluate the effect on *S. mutans* biofilm formation, 96-well microtiter plates were used. Each well contained *S. mutans* ($5 \times 10^6$ CFU/ml), and was serially diluted with test compounds and growth medium (brain heart infusion broth (BHI) with 0.5% sucrose). The controls included inoculated growth medium without test compounds. All plates were incubated at 37° C. under aerobic condition with growth estimated spectrophotometrically (660 nm) after 48 h using a microtiter plate reader. Then, the supernatant containing unattached cells was removed from each wells by aspiration, the attached biofilm mass was dissolved with 200 µl 1 N NaOH and the optical density was measured at 660 nm using the microtiter plate reader. Chlorhexidine (40 µg/ml) was used as a positive control.

To further evaluate the effect on *S. mutans* biofilm detachment, sterile 96-well microtiter plates were used where each well was inoculated with *S. mutans* ($5 \times 10^6$ CFU/ml), growth medium (BHI supplemented with 0.5% sucrose), and incubated at 37° C. under aerobic condition for biofilm formation. After 48 hours, the non-attached supernatant was aspirated and serially diluted. Test compounds were added to the preformed biofilm and incubated at 37° C. under aerobic condition. The controls included solvent without test compounds. After 30 min, the supernatant was aspirated from wells and the biofilm remaining after treatment was dissolved in 200 µl 1N NaOH, and quantitated at 660 nm using the plate reader. A chlorhexidine positive control was used. If detachment of the biofilm by action of the test compounds occurred, the spectrophotometric absorbance or optical density (OD) should show a decrease compared to the non-treated control.

The results of the comparative testing are show below in Table 1. The test results are presented in units of µg/ml for each of the compounds. In Table 1, and in the following Tables, Magnolia Bark Extract is designated as "MBE" and the chlorhexidine positive control is designated as "CHX."

TABLE 1

Comparative Effect on MIC and Biofilm (µg/ml)

| Test | Green tea | Oolong tea | Licorice | MBE | CHX |
|---|---|---|---|---|---|
| MIC growth 250 | 250 | 1000 | 250 | 7.8 | 2.5 |
| MIC biofilm formation | 250 | 250 | 250 | 7.8 | 2.5 |
| MIC biofilm detachment | >1000 | >1000 | >10000 | >1000 | >10 |

The data shown in Table 1 indicates that none of the compounds tested were more effective than chlorhexidine at removing the established biofilm. The green tea extract, licorice extract and Magnolia Bark Extract may inhibit *S. mutans* biofilm by inhibiting bacterial growth, since MICs are identical for both growth and biofilm formation. The Oolong tea did not inhibit planktonic growth, but was more effective at inhibiting the biofilm. Magnolia Bark Extract was most effective at inhibition of both growth and biofilm formation and well within an order of magnitude of the chlorhexidine positive control.

Although useful to show the comparative effect of Magnolia Bark Extract on biofilm formation and MIC growth, the foregoing test procedure may not effectively mimic the in vivo exposure of a confectionary composition such as a pressed tablet to a developing plaque biofilm. In an in vivo situation, the active could be exposed to the plaque for a defined period of time at a set frequency (for example, for 5 minutes, three times a day). Therefore, a series of comparative experiments were conducted to mimic the in vivo use of potential active ingredients. To perform the tests the saliva compositions listed below in Tables 2 and 3 were prepared.

TABLE 2

Saliva buffer composition
(filter sterilize after preparation)

| Compound | mg/L |
| --- | --- |
| Ammonium chloride | 233 |
| Calcium chloride, dihydrate | 210 |
| Magnesium chloride, hexahydrate | 43 |
| Potassium chloride | 1162 |
| $KH_2PO_4$ (monobasic potassium phosphate) | 354 |
| Potassium thiocyanate | 222 |
| Sodium citrate | 13 |
| Sodium bicarbonate | 535 |
| Dibasic sodium phosphate, $Na_2HPO_4$ | 375 |
| Urea | 173 |

TABLE 3

Supplemented Saliva Medium
(filter sterilize after preparation)

| Ingredient | wt. % |
| --- | --- |
| Whole saliva | 25 |
| Saliva buffer | 45 |
| Modified eagle medium (MEM) | 20 |
| Trypticase soy broth | 10 |

A mixed culture system that utilizes the bacteria from freshly-collected stimulated whole saliva was used. Saliva cell pellets were used to inoculate saliva-coated hydroxyapatite (S-HA) discs. The discs were placed in 24-well cell culture plates and incubated for up to 3 days. Biofilms were exposed to actives on days 2 and 3 (starting at 18 hours), and quantified on day 4. The number of bacteria was determined by spectrophotometric absorbance or optical density (OD) at 600 nm. The five phases of the experiment were: pellicle formation; bacterial attachment; biofilm growth; exposure to actives; and bacterial enumeration.

To form the pellicles, HA Discs were ultrasonically washed in deionized water and air-dried, then autoclaved. The discs were placed in a 24-well plate with 1 ml 50% sterile saliva (1 part sterile whole saliva: 1 part saliva buffer, filter sterilize after preparation) for 2 hours on slow agitation at room temperature. The saliva was suctioned and then the discs were transferred to fresh wells for bacterial attachment.

To form the biofilms, the bacterial suspension was removed, and the discs were transferred to fresh wells. One ml of supplemented saliva medium was added and the plate was placed in the incubator for overnight incubation and for the duration of the experiment (up to 72 hours).

A stock solution of 1% Magnolia Bark Extract in 60% ethanol was prepared. Magnolia Bark Extract samples were prepared having a concentration range of 125, 250, 500, and 1000 µg/ml (ppm) in a Phosphate-Buffered-Saline (PBS) solution, where the negative control was PBS and the positive control was CHX having a concentration of 0.12%. The PBS control solution had a composition as shown below in Table 4.

TABLE 4

Phosphate Buffered Saline Composition

| Ingredient | g/L |
| --- | --- |
| NaCl | 8.0 |
| KCl | 0.2 |
| $Na_2PO_4$ | 1.44 |
| $KH_2PO_4$ | 0.24 |

One ml quantities of active ingredients and controls were placed into fresh wells, and the discs were transferred to these wells for 5 minutes. The chlorhexidine control exposure was one minute, two times a day to mimic the standard mouthrinse procedure. The exposure to active ingredient was carried out at 8:00 AM, 12:00 and 4:00 PM. After the timed exposure, the solution was removed and the discs washed twice with PBS and then transferred to fresh medium. For some experiments, the medium used during the day was TSB (Tryptic Soy Broth) with a 50 µl 40% sterile sucrose solution added to each well (to give a 2% sucrose solution). The medium was not replaced after the mid-day exposure.

After overnight incubation (day 2), discs were exposed to controls and actives. On day 3 the biofilms were again exposed to tests and controls. On day 4 the discs were removed from the medium, the medium pH was measured to obtain an indication of metabolic activity, and the discs were placed into tubes with 2.5 ml PBS, vortexed for 20 sec, and then placed into the ultrasonic bath for another 20 sec. The suspension was transferred into cuvettes and the bacterial cell density determined by OD measurements at 600 nm.

The results of the pH measurements are shown below in Table 5 and the percentage reductions in OD compared to PBS control are shown below in Table 6.

TABLE 5 pH Measurements

| Test Sample | pH |
| --- | --- |
| PBS Control | 5.4 |
| CHX Control | 8.8 |
| MBE 125 | 5.2 |
| MBE 250 | 6.0 |
| MBE 500 | 7.1 |
| MBE 1000 | 7.6 |

TABLE 6

Percentage Reductions in Optical Density at 600 nm

| Test Sample | % OD reduction |
| --- | --- |
| PBS Control | 0 |
| CHX Control | 84 |
| MBE 125 ppm | −2 |
| MBE 250 ppm | 21 |

TABLE 6-continued

Percentage Reductions in Optical Density at 600 nm

| Test Sample | % OD reduction |
|---|---|
| MBE 500 ppm | 53 |
| MBE 1000 ppm | 59 |

The results shown above in Tables 5 and 6 illustrate a clear effect and dose-response of Magnolia Bark Extract on inhibition of biofilm metabolic activity (as determined by pH of the medium) and biofilm formation (OD). Chlorhexidine had a strong inhibitory effect on plaque metabolism and cell number. Magnolia Bark Extract was less effective than chlorhexidine, but the chlorhexidine concentration was slightly higher than the Magnolia Bark Extract.

To evaluate the effect of Magnolia Bark Extract in combination with the surface active agent, sodium lauryl sulfate, five active ingredient solutions were prepared using the procedures described above. The chlorhexidine control solution was prepared having a slightly reduced concentration of 0.1% (1000 ppm). Also, the MBE solutions were prepared to have a concentration of 500 ppm. Sodium lauryl sulfate was added to two of the Magnolia Bark Extract solutions to obtain SLS concentrations of 0.05% and 0.1% in the Magnolia Bark Extract solutions. The testing with Magnolia Bark Extract described above was repeated with the five solutions.

The pH test results are shown below in Table 7, where sodium lauryl sulfate is designated as "SLS."

TABLE 7 pH Measurements

| Test Sample | pH |
|---|---|
| PBS Control | 4.9 |
| CHX Control | 8.8 |
| SLS 1000 ppm | 5.7 |
| MBE 500 ppm | 7.1 |
| MBE 500 ppm/SLS 500 ppm | 5.9 |
| MBE 500 ppm/SLS 1000 ppm | 6.2 |

The percentage reductions in optical density (OD) test results are shown below in Table 8. Note that the data in the last row of this table were taken from a different experiment.

TABLE 8

Percentage Reduction in Optical Density at 600 nm

| Test Sample | % OD reduction |
|---|---|
| PBS Control | 0 |
| CHX Control | 94 |
| SLS 1000 ppm | 61 |
| MBE 500 ppm | 65 |
| MBE 500 ppm/SLS 500 ppm | 79 |
| MBE 500 ppm/SLS 1000 ppm | 70 |
| MBE 1000 ppm/SLS 500 ppm | 88 |

The results listed above in Tables 7 and 8 show that the chlorhexidine control had the highest pH and this control also had the lowest OD. Based on pH data (an indication of metabolic activity), 500 ppm Magnolia Bark Extract alone was more inhibitory than the sodium lauryl sulfate or the Magnolia Bark Extract/sodium lauryl sulfate mixtures. The OD absorbance data (bacterial number), however, indicates a synergistic effect at reducing the biofilm in test solutions combining Magnolia Bark Extract and sodium lauryl sulfate. In particular, the results show that the 1000 ppm sodium lauryl sulfate and 500 ppm Magnolia Bark Extract had similar effects in terms of plaque quantity, although Magnolia Bark Extract inhibited plaque metabolic activity to a greater extent. The Magnolia Bark Extract with sodium lauryl sulfate at 500 ppm reduced plaque growth compared to 500 ppm Magnolia Bark Extract alone. Further, the sodium lauryl sulfate at 1000 ppm was less effective than at 500 ppm in combination with 500 ppm Magnolia Bark Extract. The most effective combination was 1000 ppm of Magnolia Bark Extract in combination with 500 ppm of sodium lauryl sulfate.

Although not wishing to be bound by any particular theory regarding the active mechanism of the invention, it is possible that the reason for the paradoxical effect of decreased cell mass with increased metabolic activity of the Magnolia Bark Extract/sodium lauryl sulfate mixtures relates to the action of the sodium lauryl sulfate in allowing more rapid penetration of the Magnolia Bark Extract into the biofilm, where it has an immediate germ kill and/or growth-inhibitory effect, but the Magnolia Bark Extract is also rinsed away more easily, so the substantivity and prolonged metabolic effect is minimized.

To evaluate the germ-kill efficacy and synergist effect when two or more germ-kill actives are combined, testing was performed to determine the ratio of MBE to surface active agent. The germ-kill active and/or surface active agent were dissolved in ethanol or sterile water to give an initial concentration 0.1% to 1%. The solution was diluted with a nutrient broth to give an initial concentration of 0.05% to 0.5%, which was then serially diluted two-fold so that each subsequent dilution contained 50% of the compound concentration of the previous dilution while maintaining a constant level of nutrients for each dilution. These dilutions were inoculated with representative oral microorganisms, or incubated saliva, and incubated for 24 hours at 37° C. For each surface active agent, the lowest dilution that was not turbid was registered as the MIC. The MBC was determined by transferring 10 microliter of liquid from non-turbid tubes to fresh growth media and incubated for 48 hours. For each surface active agent, the lowest dilution that did not demonstrate growth was considered the MBC.

Table 9 below shows the MIC of various surface active agents and emulsifiers on incubated saliva.

TABLE 9

Minimum-Inhibitory-Concentration of Selected Surface Active Agents

| Sample | MIC (ppm) | Sample | MIC (ppm) |
|---|---|---|---|
| Sodium Lauryl Sulfate | 50 | Sodium Stearoyl Lactylate | >3000 |
| Betaine BF-20 | >1000 | Tween 20 | >1000 |
| Tego Betain CKD | 25 | Sucrose Stearate | >500 |
| Tego Betain ZF | 25 | Sucrose Distearate | >500 |
| Sodium Brasslate | 500 | Chlorhexidine gluconate* | 2 |
| Sodium Lauroyl Sarcosinate | 100 | | |

*used as a positive control

The results show that sodium lauryl sulfate and Cocamidopropyl Betaine are good germ-kill surface active agents, while sodium brasslate shows a moderate germ-kill efficacy. Sodium stearoyl lactylate, Polysorbate 20 (commonly known as Tween 20), Sucrose stearate, and Sucrose distearate are weak or non germ-kill actives.

To evaluate the synergistic effect of an active ingredient in combination with a surface active agent, the fractional inhibitory index (FIC) was computed according to equation (1) below:

$$FIC = [MIC_{A\text{-combined with }B}/MIC_{A\text{ alone}} + MIC_{B\text{-combined with }A}/MIC_{B\text{-alone}}] \quad (1)$$

where an FIC value of less than 1.0 is synergistic, an FIC between 1.0 and 2.0 is additive, and an FIC greater than 2.0 is antagonistic.

Table 10 below shows the MIC values for combinations of Magnolia Bark Extract/sodium lauryl sulfate and Magnolia Bark Extract/Tween-20 on *S. mutans*:

TABLE 10

Minimum-Inhibitory-Concentration of Selected Surface Active Agents

| Sample | MIC/ppm | FIC |
|---|---|---|
| Sodium Lauryl Sulfate | 100 | — |
| Magnolia Bark Extract | 25 | — |
| MBE/SLS 1/4 | 50 | 1 |
| MBE/SLS 3/2 | 25 | 0.70 |
| MBE/SLS 4/1 | 25 | 0.85 |
| MBE/Tween 20 100/100 | 25 | 1 |
| MBE/Tween 20 100/250 | >100 | >2 |
| MBE/Tween 20 100/500 | >100 | >2 |
| Chlorhexidine gluconate* | 2 | — |

The results indicate that Magnolia Bark Extract and sodium lauryl sulfate show synergistic effect (FIC<1) when combined in a ratio (MBE/SLS) between about 1/4 to about 4/1. However, Magnolia Bark Extract and Tween-20 show antagonist effect (FIC>2) when combined.

In particular, the results show that certain ratios of Magnolia Bark Extract to sodium lauryl sulfate show synergistic effects. Accordingly, the present invention contemplates pressed tablets that contain a synergistic ratio of Magnolia Bark Extract to a surface active agent. Pressed tablets having a surface active agent in a concentration range of about 25 ppm to about 500 ppm in combination with Magnolia Bark Extract will show synergistic properties for inhibiting the biofilm formation that leads to dental plaque. Further, pressed tablets having a weight ratio of at least about one part Magnolia Bark Extract to one part surface active agent will produce a synergistic anti-microbial effect in a pressed tablet. The synergistic ratio of Magnolia Bark Extract to surface active agent can range from about 1 part Magnolia Bark Extract to 1 part surface active agent up to about 4 parts Magnolia Bark Extract to 1 part surface active agent. Most preferably, the synergistic ratio is about 2 parts Magnolia Bark Extract to 1 part surface active agent. Accordingly, the present invention contemplates a wide range of pressed tablets containing a synergistic combination of Magnolia Bark Extract and a surface active agent.

EXAMPLES

The examples listed below are not intended to exclude other variations in formulations and the present invention is not limited to these formulations.

Confectionary Formulations

In an embodiment of the present invention, an effective amount for anti-microbial benefit of Magnolia Bark Extract in combination with a surface active agent, such as described above, is present in a confectionary formulation. In another aspect of the present invention, the amount of Magnolia Bark Extract is present in an amount up to 5% by weight of the confectionery product. In yet another aspect of the present invention, the amount of Magnolia Bark Extract is 1% of the weight of the confectionery product. In still another aspect, the Magnolia Bark Extract is present in the amount of 0.01% by weight of the confectionery product. Considering the potency of Magnolia Bark Extract as described in the in vitro studies above, levels as low as 0.005% by weight of the confectionery product should be effective in terms of bactericidal properties. The absolute amount of sodium lauryl sulfate in the confectionery formulation can range from about 4 mg to about 10 mg.

Confectionery compositions or products for this invention may be, for example, hard candies, chewy candies, coated chewy center candies, toffees, syrups, nougats, chocolates and tableted candies. By way of example, the hard candy is primarily comprised of corn syrup and sugar, and derives its name from the fact that it contains only 1% and 4% moisture. In appearance, these types of candies are solid, but they are actually supercooled liquids, which are far below their melting points. There are different types of hard candies. Glass types are usually clear or made opaque with dyes. Grained types of hard candies are always opaque.

By way of example, the continuous process of making the deposited glass types with a sugar base involves the spreading of corn syrup over a cylinder heated by high pressure steam. Rapid heat exchange causes the water in the syrup to evaporate. The cooked syrup is discharged, colors and flavors are added. The syrup is cooled and deposited onto a stainless steel conveyor. The syrup can be conveyed directly to hoppers which then discharge directly into molds. The candy is conveyed to batch rollers, which shapes and sizes the batch. The candy enters a former, which shapes the individual pieces into discs, balls, barrels, etc. The present invention can be made into any shape, circles, squares, triangles etc., also into animal shapes or any other novelty molding available. The candy is then cooled, wrapped and packaged.

For grained types of candy, water and sugar are the basic components being mixed with other ingredients. These are cooked at high temperatures (143-155° C., i.e. approximately 290-310° F.), causing the water to turn to steam. The product is transferred to a cooling wheel, where it is collected in about 68 kg (approximately 150 pound) batches, placed in a pulling machine to aerate the product, and the flavor is added. The candy is transferred to batch rollers where it is shaped and sized. The candy then enters a former, which shapes the individual pieces. The candy is cooled at a relative humidity of 35% and enters a rotating drum where it is coated with a fine sugar. The candy is then conveyed to the graining room for four hours at approximately 32° C. (90° F.) and 60% humidity. The entrapped air and moisture causes the product to grain.

By way of example and not limitation, the following examples in Table 11 below illustrate various embodiments of the confectionery formulations (for example candy) of the present invention.

TABLE 11

Antimicrobial Candy Formulations
(dry weight percent basis)

| Ingredient | Example 1 | Example 2 | Example 3 | Example 4 | Example 5 |
|---|---|---|---|---|---|
| Corn Syrup | 45.00 | 43.00 | — | — | 47.00 |
| Sugar | 53.49 | 50.00 | — | — | 47.00 |
| Polyalcohols | — | — | 95.00 | 94.00 | — |
| Flavor | 1.00 | 5.00 | 3.00 | 2.00 | 2.50 |
| Color | 0.50 | 1.00 | 0.60 | 0.80 | 0.50 |

TABLE 11-continued

Antimicrobial Candy Formulations
(dry weight percent basis)

| Ingredient | Example 1 | Example 2 | Example 3 | Example 4 | Example 5 |
|---|---|---|---|---|---|
| MBE | 0.01 | 1.00 | 1.20 | 3.00 | 3.00 |
| High Intensity Sweetener | — | — | 0.20 | 0.20 | — |
| Total | 100.00 | 100.00 | 100.00 | 100.00 | 100.00 |

In accordance with the invention, each of the formulations in examples 1-5 is supplemented with a surface active agent as described above. In one exemplary embodiment, each of the examples 1-5 includes about 0.001 to about 2% surface active agent.

Pressed Tablet Formulations

In an embodiment of the present invention, an effective amount for anti-microbial benefit of Magnolia Bark Extract in combination with a surface active agent, such as described above, is present in a pressed tablet formulation. In another aspect of the present invention, the amount of Magnolia Bark Extract is present in an amount up to 5% by weight of the confectionery product. In yet another aspect of the present invention, the amount of Magnolia Bark Extract is 1% of the weight of the confectionery product. In still another aspect, the Magnolia Bark Extract is present in the amount of 0.01% by weight of the confectionery product. Considering the potency of Magnolia Bark Extract as described in the in vitro studies above, levels as low as 0.005% by weight of the confectionery product should be effective in terms of bactericidal properties. The absolute amount of sodium lauryl sulfate in the confectionery formulation can range from about 4 mg to about 10 mg.

The anti-microbial compositions of the present invention are prepared by thoroughly mixing together the Magnolia Bark Extract and the surface active agent. Alternatively, these two components can be added separately, directly to the confectionary product in which they are to be provided to the consumer.

Another aspect of the present invention contemplates the incorporation of the breath antimicrobial compositions of the present invention into solid oral carriers such as slow dissolving tablets or lozenges manufactured by conventional techniques. The solid carrier is sugar or a water soluble polyhydric alcohol (polyol) such as mannitol, xylitol, sorbitol, maltitol, a hydrogenated starch hydrolysate ("Lycasin"), hydrogenated glucose, hydrogenated disaccharides, and/or hydrogenated polysaccharides, as the major ingredient, in an amount of about 85-98% by weight of the total carrier. Solid salts such as sodium bicarbonate, sodium chloride, potassium bicarbonate or potassium chloride may totally or partially replace the polyol carrier.

Tableting lubricants, in minor amounts of about 0.1 to 5% by weight, may be incorporated into the tablet or lozenge formulation to facilitate the preparation of both the tablets and the lozenges. Suitable lubricants include vegetable oil such as coconut oil, calcium stearate, magnesium stearate, amino acids, aluminum stearate, talc, starch and Carbowax.

Lozenge formulations may contain about 2% hydrocolloid as a barrier agent to provide a shiny surface as opposed to a tablet which has a smooth finish. The lozenge or tablet may optionally be coated with a coating material such as waxes, shellacs, carboxymethyl cellulose, polyethylene/maleic anhydride copolymer or Kappa-carrageenan, to further increase the time it takes the tablet or lozenge to dissolve in the mouth. The coated tablet or lozenge should be slowly dissolving, providing a sustained release rate of the active ingredients over the period of about 3 to about 15 minutes.

The anti-microbial, breath freshening compositions of the present invention are incorporated into a lozenge or tablet by conventional mixing and tableting techniques known in this field.

The present embodiment of the invention further contemplates the optional inclusion of a sweetener, flavorant, or colorant component into the tablets or lozenges containing Magnolia Bark Extract.

The sweetener component comprises any one or more sweeteners known in the art, including both natural and artificial sweeteners. The sweetener may be chosen from a wide range of materials, including water-soluble sweeteners, water-soluble artificial sweeteners, and dipeptide based sweeteners and mixtures thereof. Thus, sweeteners may be chosen from the following nonlimiting list, which includes sugars such as sucrose, glucose, corn syrup, dextrose, invert sugar, fructose and mixtures thereof; saccharine and its various salts such as the sodium or calcium salt; cyclamic acid and its various salts such as the sodium salt; free aspartame; dihydrochalcone sweetening compounds; glycyrrhizin; stevioside; monellin, thaumatin, sucralose, isomaltitol, neotame, lactitol, trehalose, lactosucrose, polydextrose, tagatose, perillartine; and sugar alcohols such as sorbitol, sorbitol syrup, mannitol, maltitol, erythritol, xylitol, and the like. Also contemplated as a sweetener is the nonfermentable sugar substitute hydrogenated starch hydrolysate (also known as Lycasin). Also contemplated is the synthetic sweetener 3,6-dihydro-6-methyl-1-1,2,3-oxathiazin-4-one-2,2-dioxide, particularly the potassium (Acesulfame-K), sodium and calcium salts thereof. Sorbitol is the preferred sweetening and bulking agent. The amount of sweetener included is an amount effective to provide the desired degree of sweetness and bulk, generally 0.001 to 70 weight % of the tablet or lozenge.

High intensity artificial sweeteners can also be used, alone or in combination, with the above. Preferred sweeteners include, but are not limited to, sucralose, aspartame, NAPM derivatives such as neotame, salts of acesulfame, alitame, stevia, saccharin and its salts, cyclamic acid and its salts, glycyrrhizinate, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Suitable flavorants include natural and artificial flavors and mints, such as oil of peppermint, menthol, oil of spearmint, vanilla, oil of cinnamon, oil of wintergreen (methyl salicylate), and various fruit flavors, including but not limited to lemon oil, orange oil, grape flavor, lime oil, grapefruit oil, apple, apricot essence, and combinations thereof. The flavorings are generally utilized in amounts that will vary depending upon the individual flavor, and may, for example, range in amounts of about 0.5% to about 3% by weight of the tablet or lozenge.

Colorants can be present in the tablets or lozenges of the present invention. Examples include pigments such as titanium dioxide, natural food colorants such as beta carotenes, betanin, turmeric, and other dyes suitable for food, drug and cosmetic applications known as F.D. & C. dyes, and the like. The materials may be incorporated in amounts of up to about 1% by weight, preferably up to about 6% by weight of the tablet or lozenge.

A representative formulation for a hard candy embodying the composition of the present invention is as follows:

TABLE 12

Antimicrobial Candy Formulations
(dry weight percent basis)

| Compound | Amount |
|---|---|
| Sorbitol | 94-98 wt. % |
| Magnesium Stearate | 0.6-0.8 wt. % |
| Colorants | 1.5-4.0 wt. % |
| Flavor | <1.0 wt. % |
| Sweetener | 0.1-0.2 wt. % |
| Magnolia Bark Extract | 25-1000 ppm |
| Surface active agent | 25-1000 ppm |

In accordance with the invention, the formulation for a hard candy is supplemented with Magnolia Bark Extract and with a surface active agent as described above. In one exemplary embodiment, the formulation includes about 0.001% to about 2.0% of a surface active agent as described above. In another exemplary embodiment, the formulation includes about 25 ppm to about 1000 ppm of a surface active agent as described above. In yet another exemplary embodiment, the formulation includes about sodium lauryl sulfate and Magnolia Bark Extract in a ratio of about 1/4 to about 4/1.

In another exemplary embodiment of the present invention, shown in Table 13, a pressed mint may be prepared from the following formulation:

TABLE 13

Antimicrobial Candy Formulations
(dry weight percent basis)

| Compound | Amount |
|---|---|
| Mint granulation | 97% |
| Ca(OH)$_2$ | 0.5% |
| Calcium stearate | 1% |
| Flavoring | 0.4% |
| Magnolia Bark Extract | 25-1000 ppm |
| Surface active agent | 25-1000 ppm |

In yet another exemplary embodiment of the present invention, shown in Table 14, confections in the form of boiled drop may be prepared from the following formulation:

TABLE 14

Antimicrobial Candy Formulations
(dry weight percent basis)

| Compound | Amount |
|---|---|
| Sugar | 73.3% |
| Corn Syrup | 25.0% |
| Ca(OH)$_2$ | 0.2% |
| Flavoring | 0.5% |
| Magnolia Bark Extract | 1.0% |
| Surface active agent | 0.01% |

The Magnolia Bark Extract and the surface active agent may be incorporated into an otherwise conventional pressed tablet formulation. The pressed tablet into which the Magnolia Bark Extract and the surface active agent are incorporated may be prepared by wet granulation, dry granulation, and direct compression methods. These methods involve conventional procedures well known to the ordinary skilled artisan. In general, wet granulation involves mixing milled powders, preparing a wet mass by blending the milled powders with a binder solution, coarse screening the wet mass and drying the moist granules, screening the granules through a 14 to 20 mesh screen, mixing the screened granules with lubricants and disintegrate agents and finally tablet compressing the mass. In contrast, dry granulation generally involves milling of powders, compression into large hard tablets to make slugs, screening of slugs, mixing with lubricants and disintegrating agents and finally tablet compression. In the direct compression method, the milled ingredients are mixed and then merely tabletted by compression.

In another exemplary embodiment of the present invention, shown in Table 15, compressed mints may be prepared from the following formulations:

TABLE 15

Antimicrobial Compressed Mint Formulations
(dry weight percent basis)

| Ingredient | Example 1 | Example 2 | Example 3 | Example 4 | Example 5 |
|---|---|---|---|---|---|
| Sorbitol | 97.63 | 97.43 | 96.83 | 95.83 | 93.83 |
| Flavor | 1.00 | 1.00 | 1.00 | 1.00 | 1.00 |
| Mg stearate | 0.97 | 0.97 | 0.97 | 0.97 | 0.97 |
| High Intensity Sweetener | 0.20 | 0.20 | 0.20 | 0.20 | 0.20 |
| MBE | 0.10 | 0.20 | 0.50 | 1.00 | 2.00 |
| SLS | 0.10 | 0.20 | 0.50 | 1.00 | 2.00 |
| Total | 100.00 | 100.00 | 100.00 | 100.00 | 100.00 |

The pressed tablet ingredients used in the invention are selected from those materials routinely used. Such ingredients primarily include sweeteners, lubricants, and optional coloring agents, binders and fillers.

Sweetening agents may be selected from a wide range of materials such as water-soluble sweetening agents, water-soluble artificial sweeteners, and dipeptide based sweeteners, including mixtures thereof. Without being limited to particular sweeteners, representative illustrations encompass: 1) Water-soluble sweetening agents such as monosaccharides, disaccharides and polysaccharides such as xylose, ribose, glucose, mannose, galactose, lactose, fructose, dextrose, sucrose, sugar, maltose, partially hydrolyzed starch, or corn syrup solids and sugar alcohols such as sorbitol, xylitol, mannitol and mixtures thereof, 2) Water-soluble artificial sweeteners such as the soluble saccharin salts, i.e. sodium or calcium saccharin salts, cyclamate salts and the like, and the free acid form of saccharin; 3) Dipeptide based sweeteners include L-aspartyl-L-phenylalanine methyl ester and related compounds.

In general, the amount of sweetener will vary with the desired amount of sweetener selected. This amount will normally be about 0.001% to about 98% by weight when using an easily extractable sweetener. The water-soluble sweeteners are preferably used in amounts of about 75% to about 98% by weight, and most preferably about 80% to about 95% by weight of the final tablet composition. In contrast, the artificial sweeteners are used in amounts of about 0.01% to about 5.0% and most preferably about 0.05% to about 0.25% by weight of the final tablet composition. These amounts are necessary to achieve a desired level of sweetness independent from the flavor level achieved from the flavor oil.

Lubricants are used in the tablet formulations in order to ease the ejection of the tablet from the die, to prevent sticking of the tablets to the punches and to limit wear on dies and punches. Tableting lubricants may be selected from a wide range of materials such as magnesium stearate, calcium stearate, zinc stearate, hydrogenated vegetable oils, talc, light mineral oil, sodium benzoate, amino acids, sodium lauryl sulfate, magnesium lauryl sulfate and mixtures thereof. Magnesium stearate is the preferred lubricant in view of its ready availability and efficient lubrication properties.

The lubricants should be in as fine a state of subdivision as possible since the smaller the particle size the greater the efficiency in the granulation. Preferred sizes are those that pass through an 80 or 100 mesh screen and most preferred through a 200 mesh screen before use. The amount of lubricant will vary broadly and is preferably from about 0.1% to about 5% by weight of the total composition.

Colorants should be selected from materials that are unaffected by higher temperatures and are considered optional ingredients in the tablet formulations. Such materials when used are employed in amounts of 0 to about 0.03% by weight of the total formulation.

Binders that are used when a wet granulation process is employed include starch, pregelatinized starch, gelatin, free polyvinylpyrrolidone, methylcellulose, sodium carboxymethylcellulose, polyvinylalcohols and so forth. Binders when used can be employed in amounts up to about 25% and preferably about 5 to about 15% by weight. Conventional fillers may also be present such as calcium sulfate, dicalcium phosphate, tricalcium phosphate, starch, microcrystalline cellulose and so forth in amounts up to about 50% by weight with preferred amounts from about 5 to 20% by weight of the final formulation.

The pressed tablet formulations are prepared by conventional means using standard techniques and equipment known to those skilled in the art. A preferred procedure of preparing the tablets of this invention involves the direct compression method described above.

In a typical embodiment the Magnolia Bark Extract and the surface active agent are blended with the tablet formulation ingredients. Once incorporated mixing is continued until a uniform mixture is obtained and thereafter the mixture is formed into suitable shapes by subjecting the formulation to a tableting operation. Compression pressures on the order up to 65 megapascals (approximately 12 tons per square inch) are normally employed.

The comestible product of the present invention is preferably provided in the form of tablets, lozenges, hard candies, chewy candies, and pressed tablets. It is emphasized that pressed tablets are more commonly referred to as pressed mints because of the flavor usually associated with such products. However, the term pressed tablets represents a better designation since the flavorant of a pressed tablet need not be mint. It is emphasized that this list of comestibles is incomplete. Other comestibles which may be formed from the components discussed above are within the contemplation of the present invention.

In the event that the comestible product is in the form of a lozenge or a pressed tablet, a barrier agent is usually present, preferably in a concentration of up to about 2 weight %. The barrier agent provides a shiny surface as opposed to a tablet which, although having a smooth finish, is usually not shiny. In a preferred embodiment, the barrier agent is a hydrocolloid. In the preferred embodiment wherein a lozenge, a tablet or a pressed tablet is utilized, these comestibles may be coated with a coating material.

Among the coating materials suitable for use in this application are waxes, shellacs, carboxymethyl cellulose, ethylene-maleic anhydride copolymers and carragennan. A coating material is used to increase the time it takes for the tablet or lozenge to dissolve in the mouth. A coated tablet or lozenge is slow dissolving, providing sustained release of the active ingredients over a longer period of time, for example 3 to 15 minutes, or sometimes even longer.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be included within the scope of the following claims.

What is claimed is:

1. A pressed tablet for freshening the breath of consumers, the pressed tablet comprising:
   (a) an oral cavity delivery agent; and
   (b) an antimicrobial agent comprising a synergistic ratio of a Magnolia bark extract and a surfactant, wherein the synergistic ratio ranges from about 1 part Magnolia bark extract to 1 part surfactant up to about 4 parts Magnolia bark extract to 1 part surfactant.

2. The pressed tablet of claim 1 wherein the surfactant comprises a bactericidal surfactant.

3. The pressed tablet of claim 1 wherein the surfactant comprises a salt selected from the group consisting of a sodium salt and an ammonium salt.

4. The pressed tablet of claim 1 wherein the surfactant comprises an anionic surfactant.

5. The pressed tablet of claim 1 wherein the surfactant comprises about 0.001% to about 2% sodium lauryl sulfate.

6. The pressed tablet of claim 1 wherein the surfactant comprises sodium lauryl sulfate.

7. The pressed tablet of claim 6 wherein the synergistic ratio of Magnolia bark extract to sodium lauryl sulfate is about 2 parts Magnolia bark extract to 1 part sodium lauryl sulfate.

8. The pressed tablet of claim 1 wherein the surfactant comprises about 0.001% to about 1.0% of the pressed tablet.

9. The pressed tablet of claim 1 wherein the oral cavity delivery agent further comprises abrasives.

10. A lozenge for freshening the breath of consumers, the lozenge comprising:
    (a) an oral cavity delivery agent; and
    (b) an antimicrobial agent comprising a synergistic ratio of a Magnolia bark extract and a surfactant, wherein the synergistic ratio ranges from about 1 part Magnolia bark extract to 1 part surfactant up to about 4 parts Magnolia bark extract to 1 part surfactant.

11. The lozenge of claim 10 wherein the surfactant comprises a bactericidal surfactant.

12. The lozenge of claim 10 wherein the surfactant comprises a salt selected from the group consisting of a sodium salt and an ammonium salt.

13. The lozenge of claim 10 wherein the surfactant comprises an anionic surfactant.

14. The lozenge of claim 10 wherein the surfactant comprises about 0.001% to about 1.0% of the lozenge.

15. The lozenge of claim 10 wherein the surfactant comprises sodium lauryl sulfate.

16. The lozenge of claim 15 wherein the synergistic ratio of Magnolia bark extract to sodium lauryl sulfate is about 2 parts Magnolia bark extract to 1 part sodium lauryl sulfate.

17. The lozenge of claim 10, comprising:
(a) a water soluble polyhydric alcohol as a carrier; and
(b) a barrier agent providing a shiny surface.

18. A confectionary composition for freshening the breath of consumers, the composition comprising:
(a) a water soluble bulk portion;
(b) at least one flavoring agent; and
(c) an effective amount of an antimicrobial agent comprising a synergistic ratio of a Magnolia bark extract and a surfactant, wherein the synergistic ratio ranges from about 1 part Magnolia bark extract to 1 part surfactant up to about 4 parts Magnolia bark extract to 1 part surfactant.

* * * * *